(12) United States Patent
Reimer et al.

(10) Patent No.: US 11,471,277 B2
(45) Date of Patent: Oct. 18, 2022

(54) PROSTHETIC TRICUSPID VALVE REPLACEMENT DESIGN

(71) Applicant: St. Jude Medical, Cardiology Division, Inc., St. Paul, MN (US)

(72) Inventors: Jay Reimer, Saint Paul, MN (US); Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 110 days.

(21) Appl. No.: 16/705,355

(22) Filed: Dec. 6, 2019

(65) Prior Publication Data
US 2020/0179109 A1    Jun. 11, 2020

Related U.S. Application Data

(60) Provisional application No. 62/777,298, filed on Dec. 10, 2018.

(51) Int. Cl.
*A61F 2/24*      (2006.01)
*A61B 17/00*   (2006.01)

(52) U.S. Cl.
CPC ...... *A61F 2/2418* (2013.01); *A61B 17/00234* (2013.01); *A61B 2017/00243* (2013.01)

(58) Field of Classification Search
CPC ........... A61F 2/24; A61F 2/2418; A61B 17/00
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |

(Continued)

FOREIGN PATENT DOCUMENTS

| | | |
|---|---|---|
| DE | 19857887 A1 | 7/2000 |
| DE | 10121210 B4 | 11/2005 |

(Continued)

OTHER PUBLICATIONS

Andersen, et al.,"Transluminal Implantation of Artificial Heart Valves", European Heart Journal, vol. 13, No. 5, May 1992, pp. 704-708.

(Continued)

*Primary Examiner* — Matthew W Schall
(74) *Attorney, Agent, or Firm* — Wei & Sleman LLP

(57) ABSTRACT

A prosthetic heart valve may include a stent, a valve assembly disposed within the stent, a flange, and a plurality of anchor arms coupled to the stent. The stent may have collapsed and expanded conditions and inflow and outflow ends. The flange may include a plurality of braided wires and may be coupled to the stent and may be positioned adjacent the inflow end of the stent in the expanded condition of the stent. Each anchor arm may have a first end coupled to the stent adjacent the outflow end of the stent, a second end coupled to the stent adjacent the outflow end of the stent, and center portions extending from the first and second ends toward the inflow end of the stent. The center portions may be joined together to form a tip pointing toward the inflow end of the stent in the expanded condition of the stent.

22 Claims, 8 Drawing Sheets

(56) References Cited

U.S. PATENT DOCUMENTS

| | | |
|---|---|---|
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |

(56) References Cited

U.S. PATENT DOCUMENTS

| | | |
|---|---|---|
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0198097 A1 | 8/2007 | Zegdi |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2016/0278923 A1 | 9/2016 | Krans et al. |
| 2017/0231761 A1 | 8/2017 | Cohen-Tzemach et al. |
| 2018/0221147 A1 | 8/2018 | Ganesan et al. |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 0154625 A1 | 8/2001 |
| WO | 01056500 A2 | 8/2001 |
| WO | 0176510 A2 | 10/2001 |
| WO | 2002036048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 2010008549 A1 | 1/2010 |
| WO | 2010096176 A1 | 8/2010 |
| WO | 2010098857 A2 | 9/2010 |

OTHER PUBLICATIONS

Andersen, H. R., "Transluminal Catheter Implanted Prosthetic Heart Valves", International Journal of Angiology, vol. 7, No. 2, Mar. 1998, pp. 102-106.

Braido, et al., "Surgical Stent Assembly," Design U.S. Appl. No. 29/375,243, filed Sep. 20, 2010.

(56) References Cited

OTHER PUBLICATIONS

Buellesfeld et al., "Treatment of Paravalvular Leaks Through Inverventional Techniques", Multimedia Manual of Cardithoracic Surgery, Department of Cardiology, Ben University Hospital, Jan. 2011, pp. 1-8.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Dewey et al., "Transapical aortic valve implantation: an animal feasibility study", The annals of thoracic surgery, No. 82, Feb. 2006, pp. 110-116.

Gössl et al., "Percutaneous Treatment of Aortic and Mitral Valve Paravalvular Regurgitation", Current Cardiology Reports, vol. 15, No. 8, Aug. 2013, pp. 1-8.

Heat Advisor, "Heart repairs without surgery. Minimally invasive procedures aim to correct valve leakage", Sep. 2004, PubMed ID 15586429.

Hijazi et al., "Transcatheter Valve Repair", CRC Press, Jan. 2006, pp. 165-186.

Hourihan et al., "Transcatheter Umbrella Closure of Valvular and Paravalvular Leaks", Journal of the American College of Cardiology, vol. 20, No. 6, Nov. 1992, pp. 1371-1377.

Huber, et al., "Direct-Access Valve Replacement", Journal of the American College of Cardiology, vol. 46, No. 2, Jul. 2005, pp. 366-370.

Knudsen et al., "Catheter-Implanted Prosthetic Heart Valves: Transluminal Catheter Implantation of a New Expandable Artificial Heart Valve in the Descending Thoracic Aorta in Isolated Vessels and Closed Chest Pigs", The International Journal of Artificial Organs, vol. 16, No. 5, May 1993, pp. 253-262.

Lightenstein et al., "Transapical Transcatheter Aortic Valve Implantation in Humans", Circulation, No. 114, Jul. 2006, pp. 591-596.

Lichtenstein, Samuel V., "Closed Heart Surgery: Back to the Future", The Journal of Thoracic and Cardiovascular Surgery, vol. 131, No. 5, May 2006, pp. 941-943.

M. J. Mack, "Minimally invasive cardiac surgery", Surgical Endoscopy, 20:S488-S492, DOI: 10.1007/s00464-006-0110-8 Presented Mar. 23, 2006.

Moazami et al., "Transluminal Aortic Valve Placement. A Feasability Study with a Newly Designed Collapsible Aortic Valve", ASAIO Journal, vol. 42, No. 5, Sep. 1996, pp. M381-M385.

Quaden et al., "Percutaneous Aortic Valve Replacement: Resection Before Implantation", European Journal of Cardio-Thoracic Surgery, vol. 27, No. 5, May 2005, pp. 836-840.

Rodríguez et al., "Guidance of Treatment of Perivalvular Prosthetic Leaks", Current Cardiology Reports, vol. 16, No. 1, Nov. 2013, pp. 1-6.

Rohde et al., "Resection of Calcified Aortic Heart Leaflets In Vitro by Q-Switched 2? μm Microsecond Laser Radiation", Journal of Cardiac Surgery, vol. 30, No. 2, Feb. 2015, pp. 157-162.

Ruiz, Carlos, "Overview of PRE-CE Mark Transcatheter Aortic Valve Technologies", Euro PCR; Powerpoint Presentation dated May 25, 2010.

Swiatkiewicz et al., "Percutaneous Closure of Mitral Perivalvular Leak", Kardiologia Polska, vol. 67, No. 7, Jul. 2009, pp. 762-764. Abstract translation included only.

TH. Walther et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb et al., "Percutaneous Aortic Valve Implantation Retrograde From the Femoral Artery", Circulation, Feb. 2006, No. 113, pp. 842-850.

Zegdi, et al., "Is It Reasonable to Treat All Calcified Stenotic Aortic Valves With a Valved Stent?", Journal of the American College of Cardiology, vol. 51, No. 5, Feb. 5, 2008, pp. 579-584.

International Search Report including the Written Opinion for Application No. PCT/US2019/064812 dated Feb. 13, 2020, 10 pages.

PROSTHETIC TRICUSPID VALVE REPLACEMENT DESIGN

CROSS-REFERENCE TO RELATED APPLICATIONS

This application claims the benefit of the filing date of U.S. Provisional Patent Application No. 62/777,298 filed Dec. 10, 2018, the disclosure of which is hereby incorporated by reference herein.

BACKGROUND

The present disclosure relates to heart valve replacements and, in particular, to collapsible prosthetic heart valves. More particularly, the present disclosure relates to collapsible prosthetic heart valves for use in the tricuspid valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has been delivered to the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Transcatheter mitral valve replacement has garnered significant attention in the past. Transcatheter tricuspid valve replacement, however, has received less attention. Typically, tricuspid valve replacement has only been performed in the past when a patient exhibited symptoms as a result of tricuspid valve disease and a replacement of the mitral valve was also necessary, with the mitral and tricuspid valve replacement being performed concurrently. While significant advances have been made in transcatheter mitral valve replacement, less progress has been seen in transcatheter tricuspid valve replacement. Because the tricuspid valve is similar in at least some aspects to the mitral valve, designs and features of prosthetic mitral valves may have relevance to the design and features of prosthetic tricuspid valves. However, important differences between the mitral and tricuspid valve structures and anatomical environments exist and it would be desirable to have a transcatheter prosthetic tricuspid valve specifically designed for replacement of the native tricuspid valve.

BRIEF SUMMARY

According to one aspect of the disclosure, a prosthetic heart valve includes a stent, a valve assembly disposed within the stent, a flange, and a plurality of anchor arms coupled to the stent. The stent may have a collapsed condition, an expanded condition, an inflow end, and an outflow end. The flange may comprise a plurality of braided wires and may be coupled to the stent and may be positioned adjacent the inflow end of the stent in the expanded condition of the stent. Each anchor arm may have a first end coupled to the stent adjacent the outflow end of the stent, a second end coupled to the stent adjacent the outflow end of the stent, and center portions extending from the first and second ends toward the inflow end of the stent. The center portions may be joined together to form a tip pointing toward the inflow end of the stent in the expanded condition of the stent.

DETAILED DESCRIPTION

As used herein, the term "inflow end," when used in connection with a prosthetic tricuspid heart valve, refers to the end of the heart valve closest to the right atrium when the heart valve is implanted in a patient, whereas the term "outflow end," when used in connection with a prosthetic tricuspid heart valve, refers to the end of the heart valve closest to the right ventricle when the heart valve is implanted in a patient. Also, as used herein, the terms "substantially," "generally," and "about" are intended to mean that slight deviations from absolute are included within the scope of the term so modified. Generally, materials described as being suitable for components in one embodiment of the disclosure may also be suitable for similar or identical components described in other embodiments.

Figure 1:
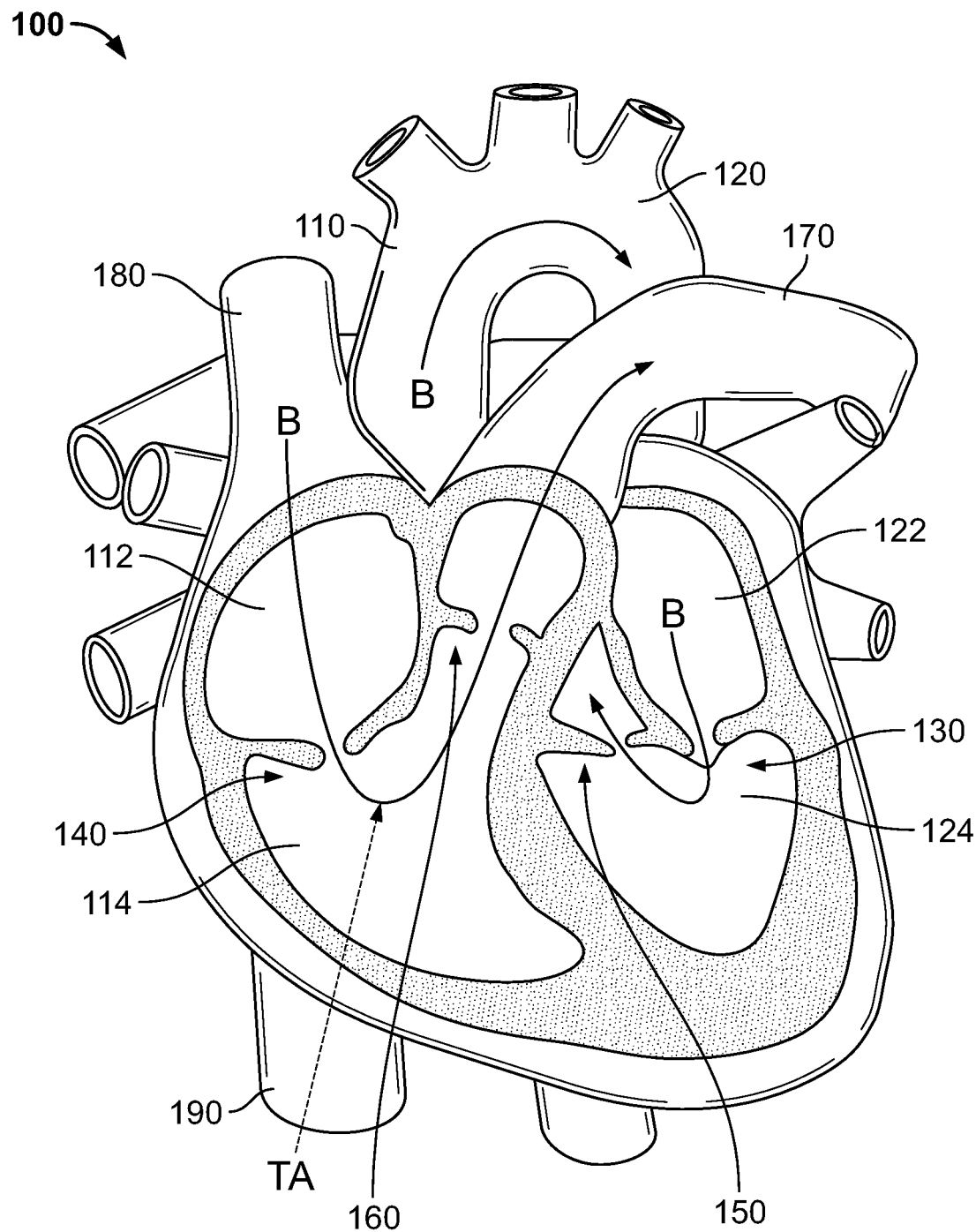
FIG. 1 is a highly schematic cutaway representation of a human heart.

FIG. 1 is a highly schematic cutaway representation of human heart 100. The human heart includes two atria and two ventricles: right atrium 112 and left atrium 122, and right ventricle 114 and left ventricle 124. Heart 100 further includes aorta 110 and aortic arch 120. Disposed between left atrium 122 and left ventricle 124 is mitral valve 130. Mitral valve 130, also known as the bicuspid valve or left atrioventricular valve, is a dual-flap valve that opens as a result of increased pressure in left atrium 122 as it fills with blood. As left atrial pressure increases above that of left ventricle 124, mitral valve 130 opens and blood passes into left ventricle 124. Similarly, disposed between right atrium 112 and right ventricle 114 is tricuspid valve 140. Tricuspid valve 140, also known as the right atrioventricular valve, is a three-flap valve that opens as a result of increased pressure in right atrium 112 as it fills with blood. As right atrial pressure increases above that of right ventricle 114, tricuspid valve 140 opens and blood passes into right ventricle 114. Blood flows through heart 100 in the direction shown by arrows B.

In addition to mitral valve 130 and tricuspid valve 140, heart 100 includes aortic valve 150, which permits one-way flow of blood from left ventricle 124 to aorta 110, and a pulmonary valve 160, which permits one-way flow of blood from right ventricle 114 to pulmonary artery 170. A dashed arrow, labeled "TA", indicates a transapical approach for implanting a prosthetic heart valve, in this case to replace tricuspid valve 140. In transapical delivery, a small incision is made between the ribs and into the apex of right ventricle 114 to deliver the prosthetic heart valve to the target site. However, other approaches for implanting a prosthetic tricuspid valve are also possible. For example, tricuspid valve 140 may be approached via superior vena cava 180 or inferior vena cava 190 using any suitable access point including, for example, the femoral vein or the jugular vein. Still other delivery approaches may be appropriate, for example including a trans-atrial approach, an axillary vein approach, or any other approach to accessing the right atrium, including a cut-down approach to gain direct access.

Figure 2A:
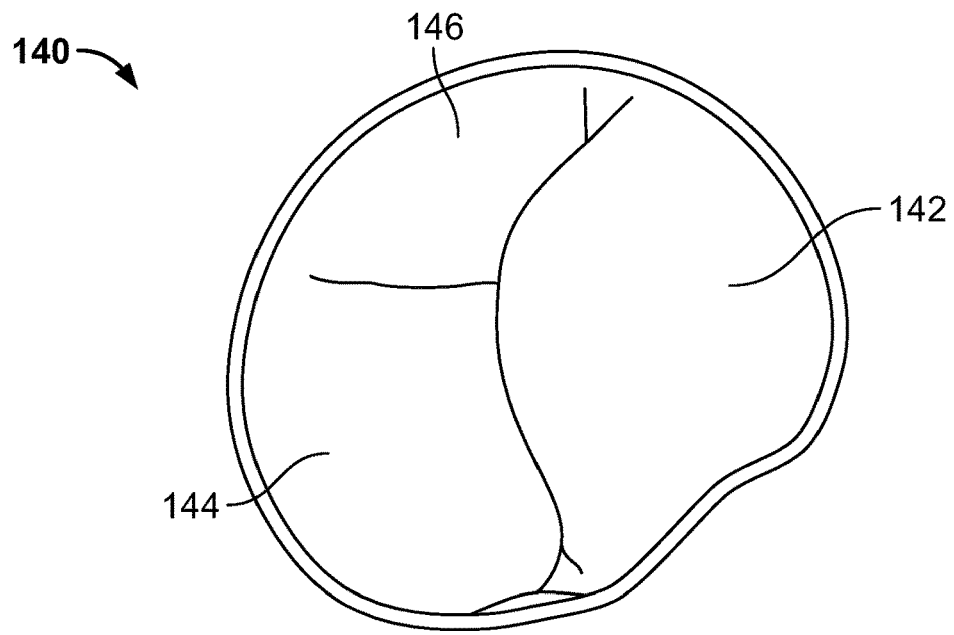
FIGS. 2A-B are highly schematic representations of a native tricuspid valve.
Figure 2B:
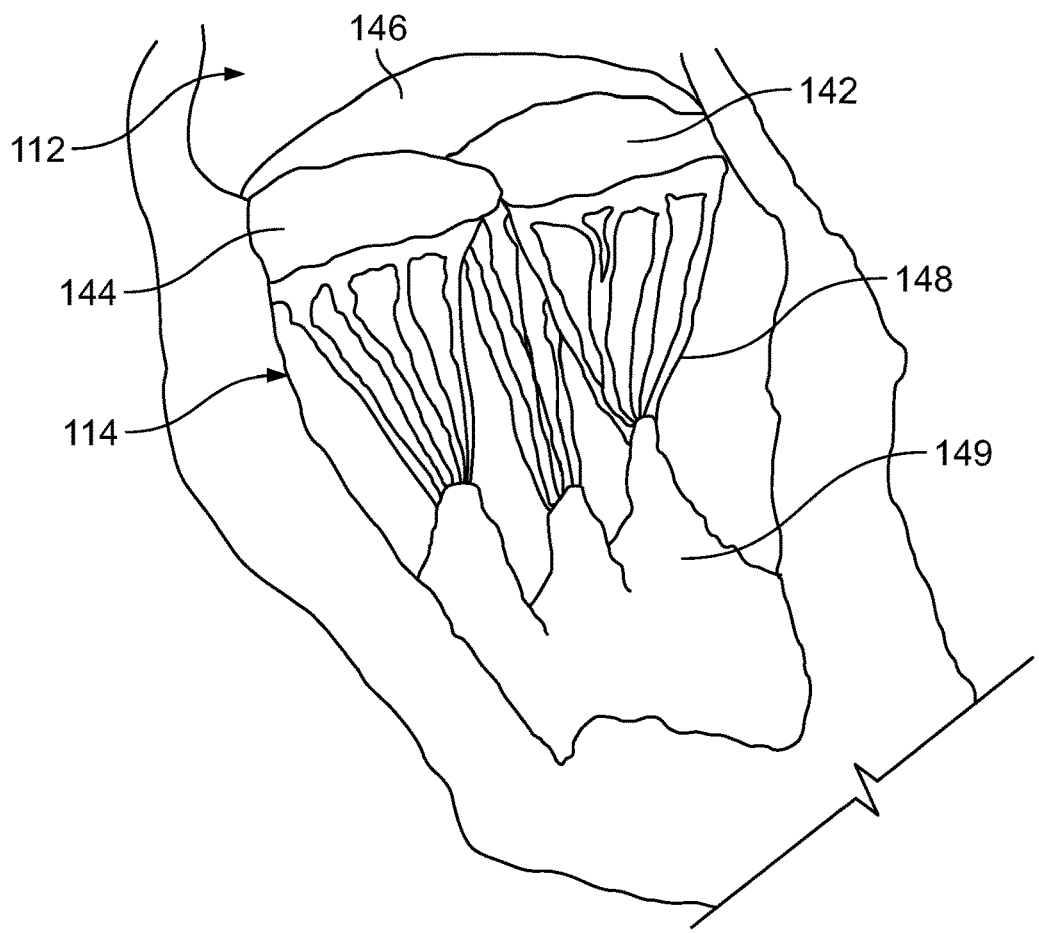

FIG. 2A is a schematic representation of native tricuspid valve 140, with FIG. 2B illustrating certain associated structures. As previously noted, tricuspid valve 140 typically includes three flaps or leaflets, including septal or medial leaflet 142, anterior leaflet 144, and posterior leaflet 146, disposed between right atrium 112 and right ventricle 114. Cord-like tendons, known as chordae tendineae 148, connect the three leaflets 142, 144, 146, to papillary muscles 149. Although heart 100 typically includes three papillary muscles 149 in right ventricle 114, more or fewer papillary muscles may be present. During atrial systole, leaflets 142, 144, 146 open, enabling blood to flow from higher pressure in right atrium 112 to lower pressure in right ventricle 114. When right ventricle 114 contracts in ventricular systole, the increased blood pressure in the chamber pushes leaflets 142, 144, 146 to close, preventing the backflow of blood into right atrium 112. Since the blood pressure in right atrium 112 is much lower than that in right ventricle 114, leaflets 142, 144, 146 attempt to evert to the low pressure regions. Chordae tendineae 148 prevent the eversion by becoming tense, thus pulling on leaflets 142, 144, 146 and holding them in the closed position.

Figure 3A:
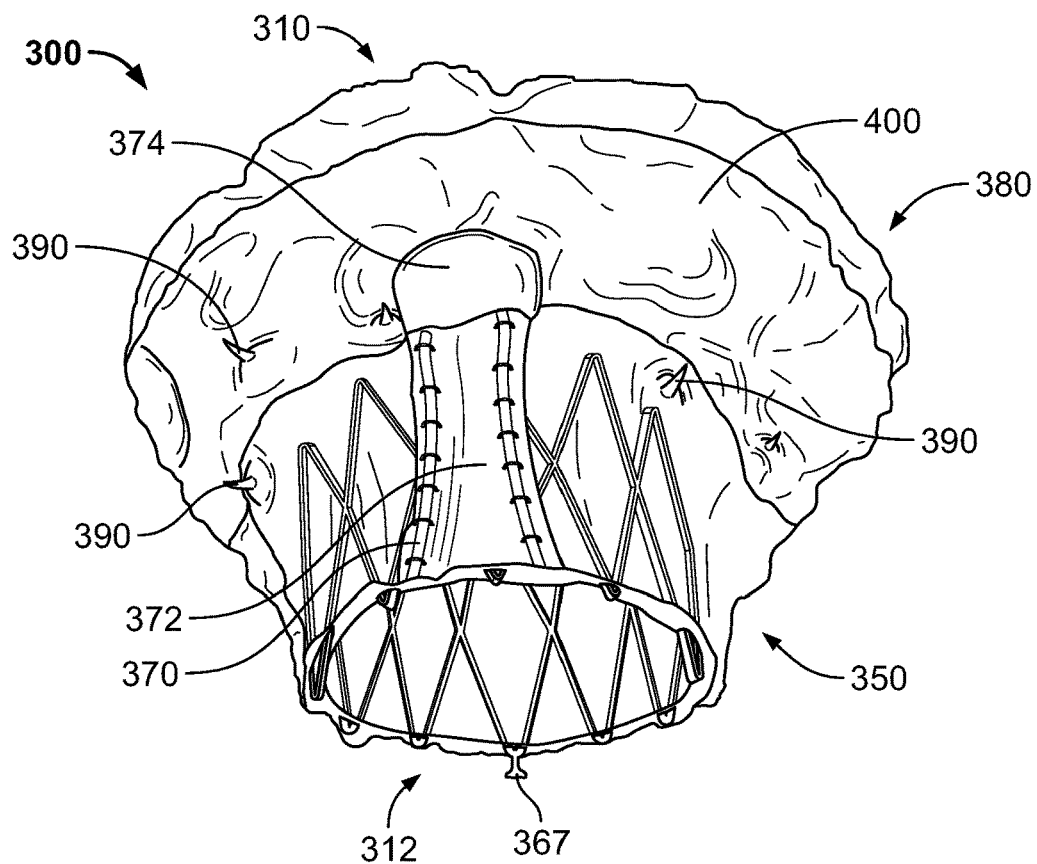
FIG. 3A is a bottom perspective view of a prosthetic heart valve.
Figure 3B:
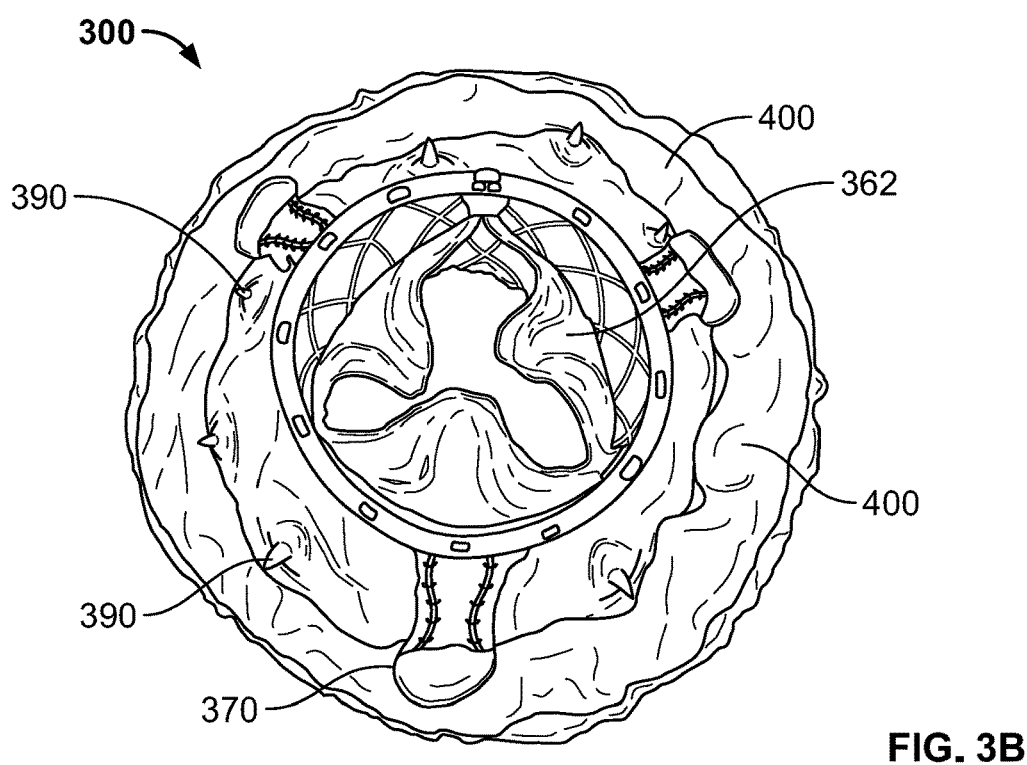
FIG. 3B is a view of the outflow end of the prosthetic heart valve of FIG. 3A.

FIG. 3A is a bottom perspective view of a prosthetic heart valve 300 according to an aspect of the present disclosure. Prosthetic heart valve 300 is shown in FIG. 3B viewing outflow end 312, and in FIG. 3C viewing inflow end 310. Prosthetic heart valve 300 is a collapsible prosthetic heart valve designed to replace the function of the native tricuspid valve of a patient, such as native tricuspid valve 140 of FIGS. 1-2B. However, it should be understood that prosthetic heart valve 300 may be suitable for use in replacing other valves, such as mitral valve 130. Generally, prosthetic valve 300 has a substantially cylindrical stent 350 and a flared flange 380, which may be an atrial flange. While in some embodiments, stent 350 may have a substantially circular cross-section, other shapes, including an oval cross-section or a D-shaped cross-section, may be appropriate.

Figure 3C:
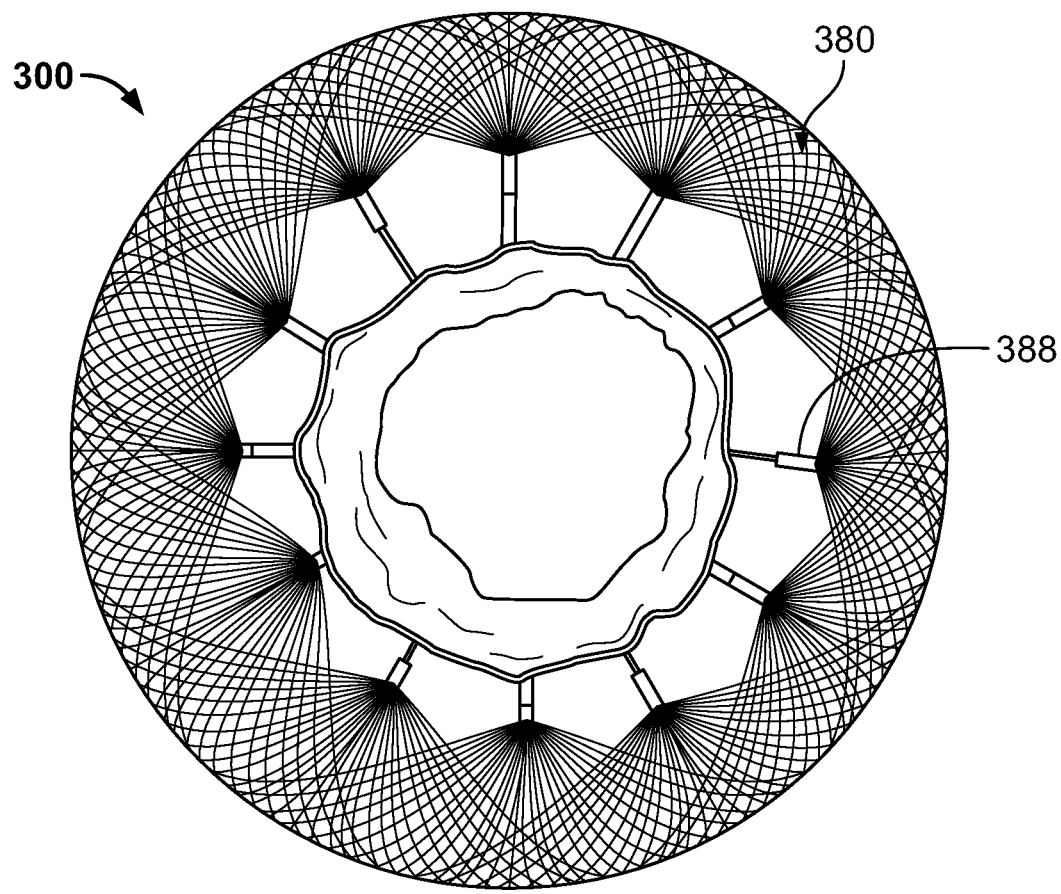
FIG. 3C is a view of the inflow end of the prosthetic heart valve of FIG. 3A.
Figure 4A:
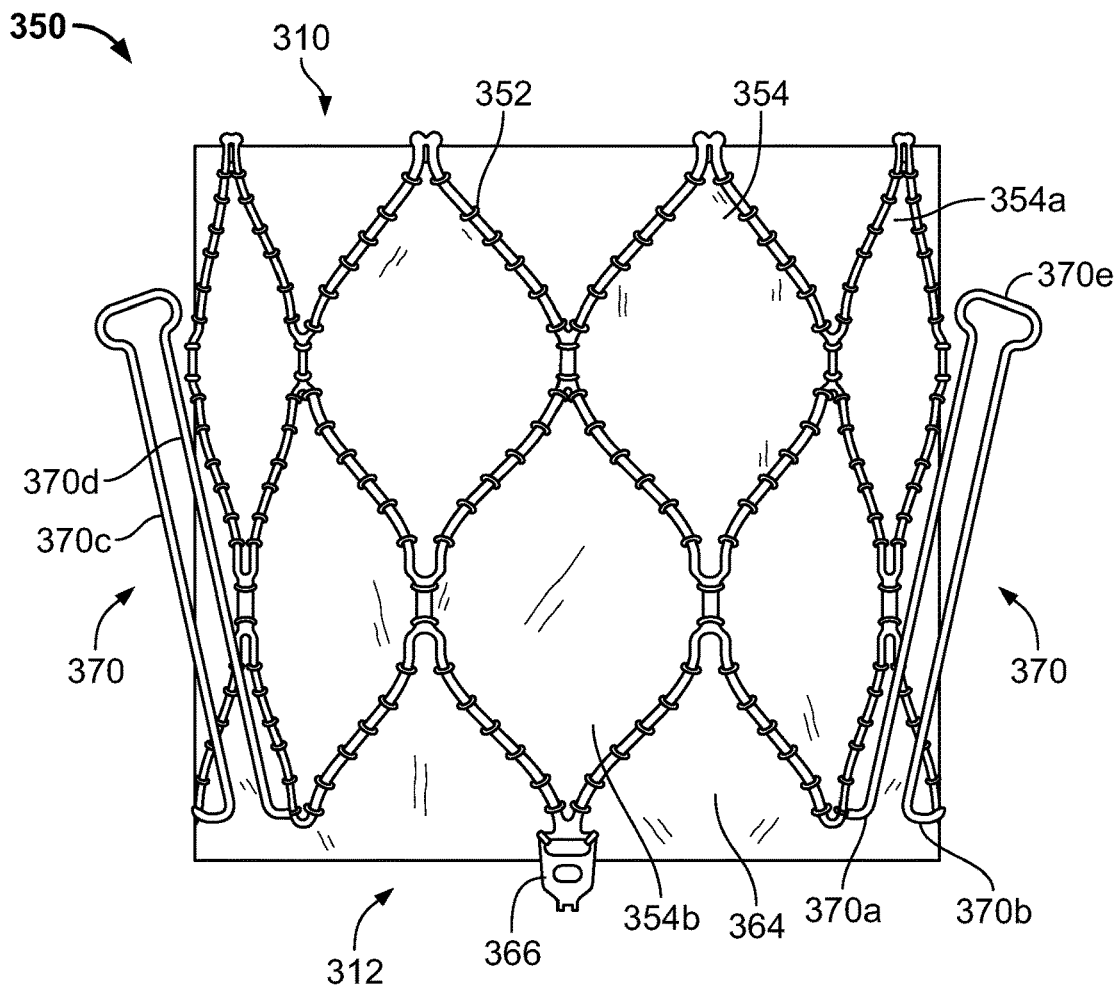
FIG. 4A is a highly schematic side view of a prosthetic heart valve.

FIG. 4A is a side view of prosthetic heart valve 300 showing stent 350 with various related structures, such as flange 380, omitted for clarity. Stent 350 may be formed from biocompatible materials that are capable of self-expansion, such as, for example, shape-memory alloys including nitinol. Stent 350 may include a plurality of struts 352 that form cells 354 connected to one another in one or more annular rows around the stent. Cells 354 may all be of substantially the same size around the perimeter and along the length of stent 350. Alternatively, cells 354 near inflow end 310 may be larger than the cells near outflow end 312, or vice versa. In the illustrated embodiment, stent 350 includes two annular rows of cells 354, including a first annular row of cells 354*a* adjacent inflow end 310, and a second annular row of cells 354*b* adjacent outflow end 312. FIG. 4A shows stent 350 as including nine substantially diamond shaped cells 354 in each row, whereas FIGS. 3A-C show the stent including twelve substantially diamond shaped cells in each row. It should be understood that more or fewer than nine or twelve cells may be provided in each row, and the cells may have shapes other than diamond shapes. Stent 350 may be expandable to exert a radial force to assist with positioning and stabilizing prosthetic heart valve 300 in the annulus of native tricuspid valve 140.

Figure 4B:
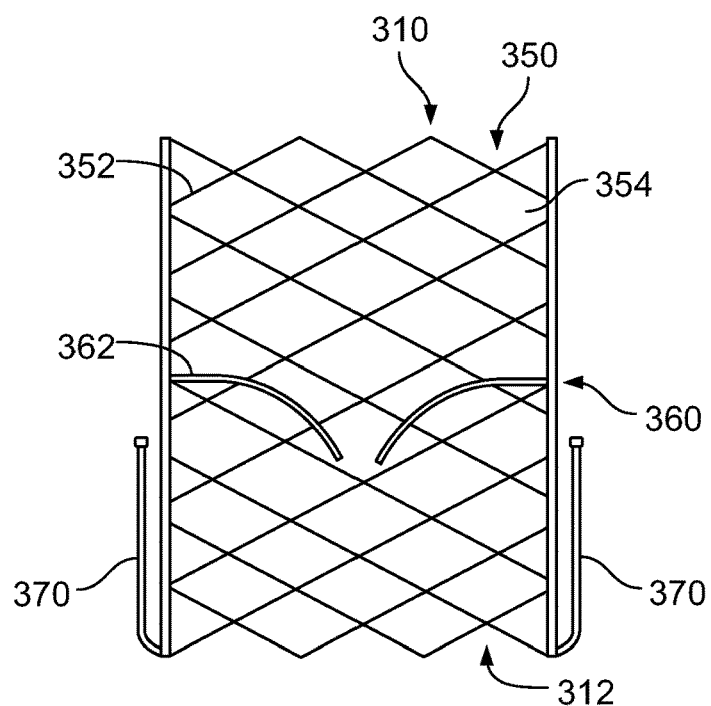
FIG. 4B is a highly schematic cross-section of the prosthetic heart valve of FIG. 4A in an expanded condition.

FIG. 4B is a highly schematic cross-section of prosthetic heart valve 300. A valve assembly 360 may be disposed within stent 350, the valve assembly including a plurality of leaflets 362 that may be attached to a cuff 364 and/or to struts 352 of stent 350. Leaflets 362 replace the function of native tricuspid valve leaflets 142, 144, 146 described above with reference to FIGS. 2A-B. That is, leaflets 362 coapt with one another to function as a one-way valve. The valve assembly 360 of prosthetic heart valve 300 may include three leaflets 362, but it should be appreciated that more or fewer than three leaflets may be suitable. Cuff 364 may cover part or all of an interior surface of stent 350, and may provide various benefits, for example including decreasing or eliminating contact between leaflets 362 and stent 350, which could otherwise cause damage to the leaflets. Cuff 364 may also assist in fixing leaflets 362 to stent 350, for example using sutures that directly couple the leaflets to the cuff. Still further, cuff 364 may assist in creating a seal between prosthetic heart valve 300 and the annulus of native tricuspid valve 140, to thereby limit paravalvular leak ("PV leak") in which blood flows from right ventricle 114 to right atrium 112 between the prosthetic heart valve and the native tricuspid valve annulus. Both cuff 364 and leaflets 362 may be wholly or partly formed of any suitable biological material, such as bovine or porcine pericardium, or polymers, such as polytetrafluoroethylene (PTFE), urethanes and the like. Cuff 364 may be positioned on the interior or luminal surface of stent 350, on the abluminal surface of the stent, or on both surfaces. Valve assembly 360 may be secured to stent 350 by suturing to struts 352 and/or to cuff 364, or by using tissue glue, ultrasonic welding, or other suitable attachment methods.

Referring now to FIGS. 3A and 4A, stent 350 may include a plurality of commissure attachment features ("CAFs") 366 to facilitate attachment of leaflets 362 to the stent. In the illustrated embodiment, CAFs 366 are positioned on the outflow end 312 of stent 350, extending in a direction away from inflow end 310. Although not shown in FIG. 4A, each CAF 366 may include a retainer 367, as shown in FIG. 3A, extending therefrom. Retainers 367 can have any shape, including substantially circular, and be configured to couple to a delivery device to prevent premature release or deployment of prosthetic heart valve 300. And while CAFs 366 are illustrated in FIG. 4A as having a single eyelet, the CAFs can have other suitable shapes, including one or more rows of eyelets formed in one or more columns, and may additional include different sized eyelets and/or elongated eyelets. Prosthetic heart valve 300 may also include stabilization or securement features to assist in maintaining the prosthetic heart valve within the native valve annulus, for example including flange 380, described in greater detail below, and stabilization or anchor arms 370. It should be noted that, although the term "anchor arms" is used herein, the arms may referred to as stabilization arms instead, and the arms may provide a stabilization and/or an anchoring function. It should further be understood that CAFs of the type described above may not be necessary. In other words, in some embodiments, the prosthetic leaflets may be directly attached to struts of the stent, instead of to a separate CAF feature.

Prosthetic heart valve 300 preferably includes three anchor arms 370, corresponding to the three leaflets 142, 144, 146 of native tricuspid valve 140. However, prosthetic heart valve 300 may include more or fewer anchor arms 370. As illustrated, anchor arms 370 are spaced at substantially equal intervals around the circumference of stent 350, although other relative spacing may be suitable. Referring to FIG. 4A, each anchor arm 370 may include a first end 370a coupled or otherwise attached to an apex of a first cell 354 in the second row of cells 354b at outflow end 312. Each anchor arm 370 may also include a second end 370b opposite first end 370a, the second end being coupled or otherwise attached to an apex of a second cell 354 in the second row of cells 354b at outflow end 312, the first and second cells being circumferentially adjacent to each other. Preferably, ends 370a and 370b of each anchor arm 370 are coupled to the cell apices that are closest to the outflow end 312 of prosthetic heart valve 300. The first and second ends 370a, 370b may transition to elongated center portions 370c, 370d, respectively, that extend toward the inflow end 310 of stent 350. Center portions 370c, 370d may transition to a tip 370e having a blunted and/or generally circular or oval shape. The tips 370e may include optional additional features to reduce trauma to adjacent tissue which the trips may contact, including, as described in greater detail below, applying materials such as polymers, tissues, fabrics, or the like to the tips. Tip 370e may have a width in a circumferential direction of stent 350 that is greater than the distance between center portions 370c, 370d.

Anchor arms 370 may be formed of any suitable material, and may be coupled to stent 350 in any suitable fashion, or otherwise may be formed integrally with the stent. In one example, anchor arms 370 are formed of nitinol and are integral with stent 350, the stent and anchor arms 370 being laser cut from the same structure. If anchor arms 370 are formed of a material having shape-memory properties, the anchor arms may be set (such as by heat setting) to have a desired shape and/or position in an unconstrained state. In use, anchor arms 370 are clipped or otherwise positioned over surfaces of the leaflets 142, 144, 146 of native tricuspid valve 140, so that the native leaflets are positioned between the anchor arms and an exterior surface of stent 350. Preferably, in use, each anchor arm 370 is positioned in contact with the center of the corresponding native leaflet 142, 144, 146. By clipping over native leaflets 142, 144, 146, particularly at their centers, anchor arms 370 can help prevent the prosthetic heart valve from migrating into right atrium 112, while also reducing movement of the native leaflets which might otherwise adversely affect proper functioning of prosthetic heart valve 300. Furthermore, if anchor arms 370 are positioned at the centers of corresponding native leaflets 142, 144, 146, the likelihood of the anchor arms interfering with chordae tendineae 148 may be reduced. As shown in FIG. 4A, about three cells 354 in the second row of cells 354b may be positioned between each pair of circumferentially adjacent anchor arms 370. However, if stent 350 includes a different number of cells, the spacing may be different. For example, in a twelve cell embodiment, such as that shown in FIGS. 3A-C, about four cells may be positioned between each pair of circumferentially adjacent anchor arms 370. In some embodiments, such as that shown in FIG. 4A, it may be preferable that anchor arms 370 are attached to stent 350 centered between circumferentially adjacent CAFs 366, such that, when implanted, the CAFs of prosthetic heart valve 300 are substantially aligned with the commissures of native valve leaflets 142, 144, 146 when anchor arms 370 are clipped over center portions of the corresponding native leaflets.

As noted above, anchor arms 370 may clip over native leaflets 142, 144, 146 when prosthetic heart valve 300 is implanted in the annulus of tricuspid valve 140. The blunted shape of tips 370e may help to reduce the likelihood that anchor arms 370 would damage native tissue at or near tricuspid valve 140. However, additional features may be provided to further reduce the likelihood of anchor arms 370 damaging native tissue. For example, as best illustrated in FIG. 3A, anchor arms 370 may include one or more layers of a buffer or other material. In the illustrated example, anchor arm 370 is covered with a first layer 372 of buffer material that is sutured or otherwise coupled to the anchor arm. First layer 372 may be one or more layers of tissue, for example bovine or porcine pericardium. In some embodiments, anchor arm 370 may be completely or substantially completely covered by first layer 372, which may include two or more layers that sandwich the anchor arm therebetween. First layer 372 can extend over both center portions 370c, 370d and over tip 370e of anchor arms 370. A second layer 374 of a buffer material may be provided on the tip 370e of anchor arm 370. The tip 370e of anchor arm 370 may be more likely to damage native tissue, and second layer 374 may further reduce the likelihood of such damage. In the illustrated embodiment, second layer 374 is formed from a biocompatible polymer fabric or sheet material, such as PTFE, and overlies first layer 372. It should be understood that, although first layer 372 is described as being formed of tissue, and second layer 374 is described as being formed of a polymer fabric or sheet material, either layer may be formed of either material, or of a combination of both materials. In some embodiments, second layer 374 may be provided without first layer 372, and in other embodiments, the first layer may be provided without the second layer. The first layer 372 and the second layer 374 may increase the area of contact between anchor arm 370 and the corresponding native leaflets 142, 144, 146, and may be softer than the center portions 370c, 370d and tip 370e of the anchor arm, thus reducing the likelihood that the native tissue is damaged from interaction with the anchor arms.

Figure 4C:
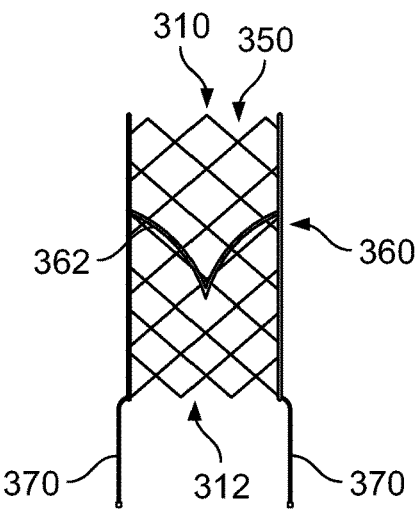
FIG. 4C is a highly schematic cross-section of the prosthetic heart valve of FIG. 4A in a collapsed condition.

As noted above, anchor arms 370 are preferably made from a shape-memory alloy. By using a shape-memory alloy, the anchor arms 370 may be set, for example by heat setting, to take the illustrated shape and/or position in the absence of applied forces. However, forces may be applied to anchor arms 370 and to prosthetic heart valve 300 generally to reduce the radial size and/or bulk of the prosthetic heart valve when in the collapsed condition, which may facilitate intravascular (or other minimally invasive) delivery of the prosthetic heart valve via a delivery device (not shown). For example, as shown in FIG. 4C, stent 350 may be transitioned to the collapsed condition, with tips 370e of anchor arms 370 being distorted or "flipped" to point away from inflow end 310 rather than toward the inflow end. Prosthetic heart valve 300 may be maintained in the collapsed condition, for example by a surrounding sheath of a delivery device (not shown), as prosthetic heart valve 300 is delivered to native tricuspid valve 140. When in a desired position relative to native tricuspid valve 140, prosthetic heart valve 300 may be released from the delivery device. As the constraining forces of the surrounding sheath are removed from prosthetic heart valve 300, it begins to transition to the expanded condition shown in FIG. 4B, while anchor arms 370 transition to their preset shape. Since anchor arms 370 are shape-set so that their tips 470e point toward inflow end 310, the anchor arms revert to that shape when released from the delivery device. As the tips 370e of anchor arms 370 transition from pointing away from inflow end 310 to pointing toward the inflow end, native tricuspid valve leaflets 142, 144, 146 are captured between the anchor arms and the abluminal surface of stent 350. Distorting or flipping anchor arms 370 to point away from inflow end 310 while prosthetic heart valve 300 is maintained in the collapsed condition may reduce the profile of the collapsed valve. However, it should be understood that this flipping of anchor arms 370 is not required. In other words, when stent 350 is transitioned into the collapsed condition, the tips 370e of anchor arms 370 may instead be kept pointing toward inflow end 310, which may slightly increase the radial profile of the collapsed valve, but also decrease the total longitudinal length of the collapsed valve, which may be desirable in some circumstances.

Although anchor arms 370 are shown in the figures as having a particular length, the lengths may be greater or smaller than shown. For example, if it is desired that anchor arms 370 only clip onto native leaflets 142, 144, 146, the anchor arms may be relatively short. However, if it is desired that anchor arms 370 clip onto native leaflets 142, 144, 146 and also engage the native annulus for additional stabilization, the anchor arms may be relatively long. Still further, although anchor arms 370 are shown as being coupled to apices of two adjacent cells 354 in the second row 354b, other attachment positions may be suitable. For example, anchor arms 370 may be attached to a single cell 354 in the second row 354b, for example so that first and second ends 370a, 370b are positioned within a cell on either side of the apex. Further, anchor arms 370 may be attached to any desired portions of stent 350 in any suitable fashion. And while anchor arms 370 are shown as generally symmetrical, this is not necessary. For example, in some embodiments, different anchor arms 370 may have different lengths, may be attached at different locations (e.g. attached to cells in different rows), and may have unequal spacing around the perimeter of the stent.

Figure 5A:
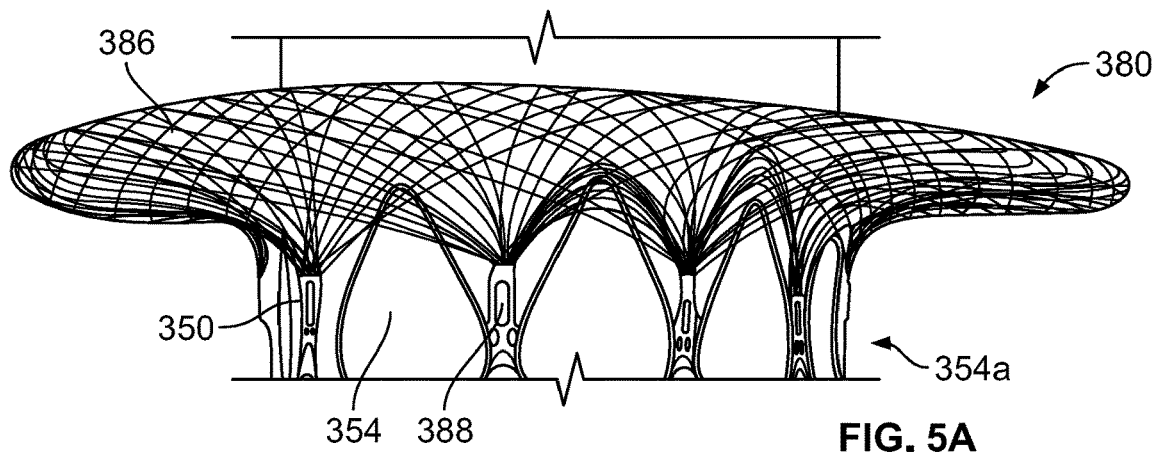
FIG. 5A is a bottom perspective view of a flange for use with a prosthetic heart valve.

While FIG. 4A illustrates one type of stabilization feature in the form of anchor arms 370, a second type of stabilization feature, in the form of flange 380, is omitted from FIG. 4A but illustrated in FIGS. 3A-C. Generally, flange 380, which may also be referred to as an atrial flare, is intended to be positioned in right atrium 112 adjacent the annulus of native tricuspid valve 140, with the size and shape of the flange helping to prevent migration of prosthetic heart valve 300 into right ventricle 114 and to further assist in providing a seal against the annulus. Flange 380 may be formed of a material braided to create various shapes and/or geometries to engage tissue. FIG. 5A illustrates flange 380 attached to a portion of stent 350 in an intermediate stage of manufacture of prosthetic heart valve 300, with valve assembly 360, anchor arms 370, and any coverings, such as cuffs or tissue layers, omitted for purposes of clarity. Referring to FIGS. 3A-C and 5A, flange 380 includes a plurality of braided strands or wires 386 arranged in three dimensional shapes. In one example, wires 386 form a braided metal fabric that is resilient, collapsible and capable of heat treatment to substantially set a desired shape. One class of materials which meets these qualifications is shape-memory alloys, such as nitinol. Wires 386 may comprise various materials other than nitinol that have elastic and/or shape memory properties, such as spring stainless steel, tradenamed alloys such as Elgiloy® and Hastelloy®, CoCrNi alloys (e.g., tradename Phynox), MP35N®, CoCrMo alloys, or a mixture of metal and polymer fibers. Depending on the individual material selected, the strand diameter, number of strands, and pitch may be altered to achieve the desired shape and properties of flange 380. In the expanded condition of flange 380, the porosity of the braided fabric is preferably such as to not interfere with the flow of blood through prosthetic heart valve 300 when the leaflets 362 thereof are in the open position.

Flange 380 may include a plurality of groups of individual wires 386 that are bunched together at regular intervals around stent 350 to attach the flange to the stent. In the embodiment illustrated in FIG. 5A, groups of individual wires 386 are attached to portions of stent 350 where a first cell 354 in the first row of cells 354a joins a circumferentially adjacent cell in the first row of cells. Thus, in some examples, the number of bunches of individual wires 386 coupling flange 380 to stent 350 is equal to the number of cells 354 in the first circumferential row of cells 354a, although this one-to-one relationship is not a requirement. The individual wires 386 in a particular group or bunch may be coupled together via a coupling tube 388 or other structure that is also attached to stent 350. Although the groups of individual wires 386 are shown in FIG. 5A as being coupled between adjacent cells 354 in the first row of cells 354a, it should be understood that the groups of individual wires may instead be attached to other portions of stent 350, for example between adjacent cells in the second row of cells 354b, or to any desired apices of the cells. Flange 380 may additionally or alternatively be coupled to stent 350 by sutures, ultrasonic welds, glue, adhesives, or other suitable means. Examples of coupling tubes 388 and other suitable structures for coupling flange 380 to stent 350 are described in greater detail in U.S. Provisional Patent Application No. 62/745,528, titled "Braid Connections for Prosthetic Heart Valves" and filed on Oct. 15, 2018, the disclosure of which is hereby incorporated by reference herein.

Flange 380 may extend around the outside of stent 350 from the points at which the flange is connected to the stent to inflow end 310 of prosthetic heart valve 300. The shape of flange 380 in an unconstrained condition may be generally disc-shaped or cylindrical, although other shapes including toroid-shaped, trumpet-shaped, elliptical, conical, and/or frustoconical may be suitable. Flange 380 may be preset to take the desired shape in the absence of applied forces. As with stent 350, flange 380 may be collapsed to a decreased profile to facilitate minimally invasive delivery.

Figure 5B:
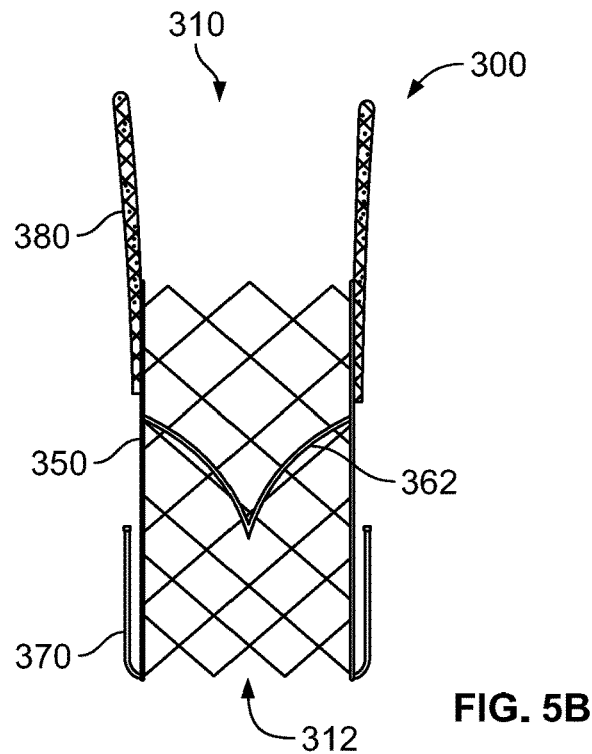
FIG. 5B is a highly schematic cross-section of the prosthetic heart valve of FIG. 3A in a collapsed condition.

For example, prosthetic heart valve 300 may be transitioned from an expanded condition to a collapsed condition and maintained in the collapsed condition by a surrounding sheath of a delivery device. As shown in FIG. 5B, flange 380 may collapse radially inwardly and become substantially cylindrical and/or significantly less flared than in the expanded condition. In the collapsed condition, flange 380 extends away from outflow end 312, so that much, most, or all of the flange does not radially overlap with stent 350, reducing the radial profile of prosthetic heart valve 300 when it is collapsed. It should be noted that, in FIG. 5B, prosthetic heart valve 300 is illustrated with the tips 370e of anchor arms 370 pointing toward inflow end 310 in the collapsed condition, which, as noted above, is an alternative to the collapsed condition shown in FIG. 4C. The individual bunches of wires 386 of flange 380 may extend at an angle from stent 350 based at least in part by the angle at which coupling tubes 388 extend from the stent. The angle of each bunch of wires 386 may be substantially the same which my assist in forming a generally circular flange 380. However, in some embodiments, it may be preferable for flange 380 to have a substantially oval shape in the expanded condition. One way to achieve such an oval shape for flange 380 is by providing different angles of coupling tubes 388 around the perimeter of the stent to create an oval shape. Exemplary angles for coupling tubes 380 may include, for example, about 30 degrees, about 45 degrees, or about 60 degrees relative to stent 350, although other angles may be suitable.

FIG. 5A illustrates flange 380 without any additional materials covering or otherwise incorporated into the flange. However, as shown in FIGS. 3A-C, one or more surfaces of flange 380 may be covered by material(s), such as tissue and/or fabric, including any of the materials described above as being suitable for leaflets 362 and/or cuff 364. For example, the surface of flange 380 intended to contact the annulus of native tricuspid valve 140 may be partially or completely covered with tissue and/or fabric, which may help prevent PV leak and/or facilitate tissue ingrowth to further secure prosthetic heart valve 300 after implantation. In other embodiments, similar layers of material may be provided on the surface of flange 380 opposite the surface intended to contact the annulus of native tricuspid valve 140. Still further, layers of tissue and/or fabric may be provided on both surfaces of flange 380. Alternatively or additionally, tissue and/or fabric layers may be provided between the opposing surfaces of flange 380, particularly when the flange is folded over itself so that an interior space is provided between the opposing surfaces of the flange.

FIGS. 3A-C also illustrate a third type of stabilization feature in the form of cleats or barbs 390. In the illustrated embodiment, barbs 390 are positioned at discrete locations in the circumferential direction around the outer perimeter of stent 350, the barbs including sharp tips that point radially outwardly from the longitudinal center of the stent. Barbs 390 may extend radially outwardly from stent 350 a short distance compared to the distance which flange 380 extends radially outwardly from the stent. If included, barbs 390 may function to pierce or otherwise engage native tissue at or near the annulus of native tricuspid valve 140, further stabilizing prosthetic heart valve 300 upon implantation. Because stent 350 is already intended to be in close contact with the annulus of native tricuspid valve 140, barbs 390 need not be long in order to effectively engage the native tissue. In some embodiments, barbs 390 are formed integrally with the stent, although in other embodiments the barbs could be formed separately and attached to the stent. Barbs 390 may be provided in any desired position and in any desired number on stent 350. For example, one or more barbs 390 may be provided for each cell 354 in the first row of cells 354a, including at positions at either or both apices of each cell, or at positions where adjacent cells in the first row of cells join one another. One or more barbs 390 may also be provided for each cell 354 in the second row of cells 354b, including at either or both apices of each cell, or at positions where adjacent cells in the second row of cells join one another. In yet another example, barbs 390 may be provided on less than each cell 354 in the first row of cells 354a and/or the second row of cells 354b. Barbs 390 may extend substantially orthogonally to the center longitudinal axis of stent 350, or may otherwise be flared or curved in any desired direction. In one example, one or more barbs 390 may curve between stent 350 and the sharp tip of the barb in a direction toward inflow end 310, since prosthetic heart valve 300 may experience the largest force in the direction of right atrium 112 when leaflets 362 coapt with one another and right ventricle 114 contracts. In addition, if barbs 390 curve toward inflow end 310, the barbs may be able to fold or otherwise readily collapse when prosthetic heart valve 300 is transitioned into the collapsed condition, which may reduce the likelihood of the barbs damaging components of the prosthetic heart valve and/or structures of the delivery device. However, other curvatures may be provided as desired, or omitted entirely. Depending on the particular delivery approach, a curvature of barbs 390 may be chosen that does not significantly restrict the ability to re-sheath prosthetic heart valve 300 into a delivery device if, upon partial deployment, it is determined that the prosthetic heart valve should be re-collapsed into the delivery device so that the prosthetic heart valve may be repositioned and re-deployed. Still further, although barbs 390 are shown and described as being integral with or otherwise attached to stent 350, barbs may be additionally or alternatively provided on flange 380. For example, barbs 390 may be integrally formed with the braid of flange 380, or may be separately attached thereto, particularly on the surface of the flange intended to contact the annulus of native tricuspid valve 140. If barbs 390 are provided on flange 380, as with barbs on stent 350, they may be provided in any desired number and at any desired locations expected to contact native tissue to provide increased stabilization of prosthetic heart valve 300. If barbs 390 are provided on flange 380, they may be less stiff than if barbs are provided on stent 350, although this is not required. One way to provide barbs 390 on flange 380 may be to shape-set, for example by heating, a wire in a general U-shape, and suture the wire to the braid of the flange.

Although barbs 390 are described above as being attached to stent 350 and/or flange 380, it may be preferable instead to provide the barbs on coupling tubes 388 (or other suitable connectors that couple the flange to the stent), with the sharp end of the barbs pointing radially outwardly from the longitudinal center of the stent, with any desired curvature as described above. In addition, although the barbs 390 are described as being sharp, which may assist in piercing tissue to provide increased stability, the barbs may alternatively be blunted, with the blunted barbs providing increased friction to provide increased stability. Still further, although the barbs 390 are generally shown as being symmetrically placed around the perimeter of the prosthetic heart valve 300, such symmetry is not necessary. For example, barbs 390 could be placed or omitted from strategic locations on the prosthetic heart valve 300 depending on what anatomical structures are anticipated to be positioned adjacent those strategic locations. For example, it may be desirable to omit barbs 390 from locations on the prosthetic heart valve 300 expected to be adjacent coronary arteries.

Figure 6:
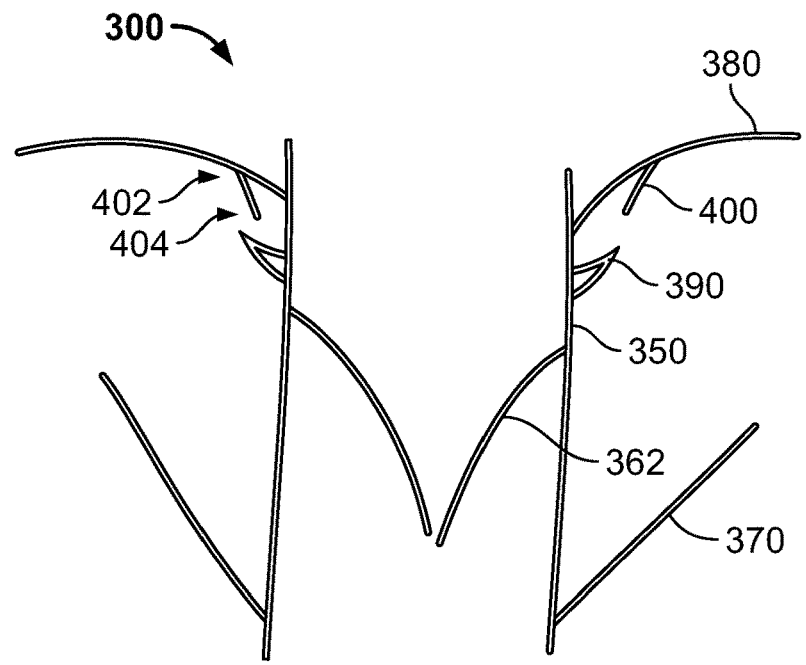
FIG. 6 is a highly schematic cross-section of the prosthetic heart valve of FIG. 3A in an expanded condition.

FIG. 6 is a schematic longitudinal cross-section of prosthetic heart valve 300 in the expanded condition, illustrating the three stabilization features described above, including anchor arms 370, flange 380, and barbs 390. FIG. 6 additionally illustrates a feature for mitigating PV leak in the form of parachute 400. Parachute 400 is also illustrated in FIGS. 3A-B. Parachute 400 may be formed from tissue and/or fabric, including any of the materials described above in connection with leaflets 362 and/or cuff 364. In the illustrated embodiment, parachute 400 is a substantially rectangular strip of tissue that has a first edge 402 coupled to the surface of flange 380 intended to contact the annulus of native tricuspid valve 140. First edge 402 may be coupled along most or all of its length to flange 380, for example by a continuous suture line. Parachute 400 may include a second edge 404 opposite first edge 402 that is also coupled to the surface of flange 380 intended to contact the annulus of native tricuspid valve 140. However, second edge 404 may be coupled to flange 380 only at spaced locations along its length, for example by individual suture stitches. Preferably, second edge 404 is coupled to flange 380 at positions radially inward from first edge 402. With this configuration, one or more pockets of space are created between parachute 400 and adjacent portions of flange 380 and/or stent 350, with openings to those pockets being defined between the intermittent connections of second edge 404 to flange 380, the openings facing the outer surface of stent 350. When prosthetic heart valve 300 is implanted and leaflets 362 are coapted so that the valve is closed, blood flowing in the retrograde direction between the outside of stent 350 and the native valve annulus may enter the openings to the pocket(s), which may cause parachute 400 to billow outwardly and create a better seal between prosthetic heart valve 300 and the annulus of native tricuspid valve 140, reducing or eliminating PV leak.

Although parachute 400 is described above as a single piece of rectangular material, other options may be suitable. For example, the material need not be rectangular, need not be a single continuous piece, and could take any shape and/or include any number of individual pieces joined together that allow for the parachute functionality described above. Also, while parachute 400 is shown as being wrapped around the entire perimeter of stent 350, in some embodiments, a single section of parachute or multiple individual sections of parachute may be provided along less than the entire perimeter of the stent, for example in regions particularly susceptible to PV leak. Still further, although parachute 400 is illustrated in FIGS. 3A-B and 6 as being coupled to flange 380, the parachute may instead be attached to the exterior surface of stent 350 near the flange. Parachute 400 may be attached to stent 350 in substantially the same way as described above for attachment to flange 380, with first edge 402 continuously or substantially continuously attached to the stent to form a closed side of the parachute, and second edge 404 attached to the stent only at intermittent locations to define openings into which blood may flow. In yet another embodiment, first edge 402 of parachute 400 may be coupled to flange 380 with second edge 404 coupled to stent 350. In some embodiments, one parachute 400 may be provided on flange 380, with a second parachute provided on the exterior surface of stent 350. Still further, it should be understood that the intermittent attachments of second edge 404 to flange 380 or stent 350 may function to stop parachute 400 from everting by action of retrograde blood flow. However, depending on the specific material used for parachute 400 and the methods of attachment and relative geometries, the parachute may be able to resist everting even if second edge 404 is not directly attached to the flange or stent. Although it is noted above that parachute 400 may be provided on stent 350 and/or flange 380, it should also be understood that more than one parachute may be provided on the stent, and more than one parachute may be provided on the flange. Although additional parachutes 400 may increase the resistance to PV leak, additional material typically increases the profile of prosthetic heart valve 300 in the collapsed condition, and it is generally desirable to limit the size of the profile in the collapsed condition. Still further, it should be understood that, when parachute 400 is coupled to flange 380, an intervening layer of material may be positioned between the parachute and the surface of flange 380 to which the parachute is coupled, which may provide a better seal if the spacing of the wires 386 of the flange would otherwise allow blood to flow through the flange. If, on the other hand, parachute 400 is coupled to stent 350, cuff 364 may serve a similar purpose as the above-mentioned intervening layer of material.

Figure 7:
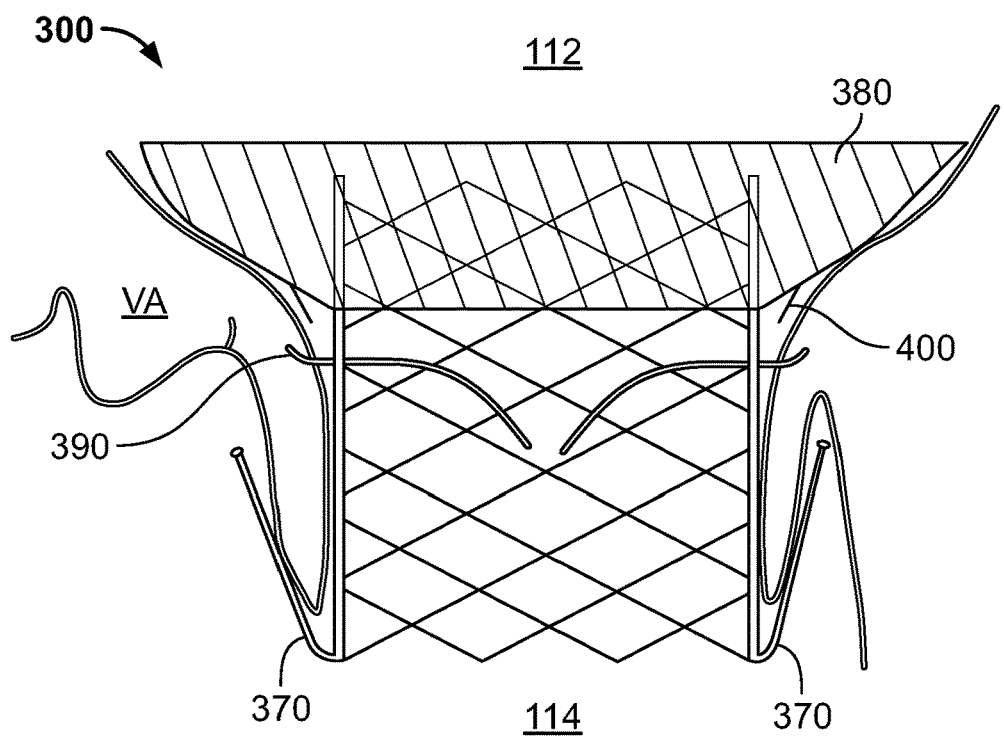
FIG. 7 is a highly schematic representation of the prosthetic heart valve of FIG. 3A implanted into a native tricuspid valve annulus.

FIG. 7 is a highly schematic representation of prosthetic heart valve 300 implanted into the valve annulus VA of tricuspid valve 140. As shown in FIG. 7, upon implantation of prosthetic heart valve 300, anchor arms 370 are clipped around the native leaflets of tricuspid valve 140. Although two anchors 370 and two corresponding native leaflets are shown in FIG. 7, it should be appreciated that a third anchor arm and the third native leaflet are omitted from FIG. 7. Barbs 390 are also illustrated as piercing into valve annulus VA to better secure prosthetic heart valve 300 within the valve annulus. Flange 380 is able to closely conform to the tissue surfaces at and adjacent to valve annulus VA at least in part due to the flexibility provided by forming the flange from braided nitinol, although other configurations and other materials may be able to provide similar conformability. Further, as shown in FIG. 7, parachute 400 is positioned at or adjacent valve annulus VA so that, if blood flows from right ventricle 114 toward right atrium 112 between the outer surface of stent 350 and the inner surface of the valve annulus, that blood will tend to enter the pocket(s) of the parachute and billow the parachute outwardly to reduce or eliminate blood passing into the right atrium from the right ventricle around the outside of prosthetic heart valve 300.

As noted above, prosthetic heart valve 300 is preferably intended for replacement of tricuspid valve 140, although it may be effective at replacing native mitral valve 130, with or without alterations such as providing two anchor arms to clip over the two mitral valve leaflets instead of three anchor arms to clip over the three tricuspid valve leaflets. However, certain elements of prosthetic heart valve 300 also make it particularly suited for replacing tricuspid valve 140. For example, although it may not be clear from FIG. 1, which is not drawn to scale, right ventricle 114 is generally smaller than left ventricle 124, at least in part due to the fact that the left ventricle pumps blood to the entire body, whereas the right ventricle pumps blood only to the lungs. As a result, while a mitral valve prosthesis may be able to extend a relatively large distance into left ventricle 124, prosthetic heart valve 300 may include features that allow it to extend only a relatively small distance into right ventricle 114. For example, as best illustrated in FIGS. 4A and 7, anchor arms 370 are attached to stent 350 at outflow end 312, so that there is little or no additional structure beyond the point of attachment of the anchor arms to the stent. As a result, when anchor arms 370 clip over the native leaflets 142, 144, 146 of tricuspid valve 140, there is little or no additional structure extending beyond the native leaflets into right ventricle 114. Another anatomical difference between left ventricle 124 and right ventricle 114 is that, typically, there is no native leaflet belly in the right ventricular outflow tract ("RVOT"), which may make it easier to capture the native leaflets with a prosthetic tricuspid valve compared to the mitral valve. Further, the shape of the RVOT is different than the shape of the left ventricular outflow tract ("LVOT"). For example, the native pulmonary valve is farther away from the native tricuspid valve, compared to the distance between the native aortic valve and the native mitral valve. As a result, it may be less likely that a prosthetic tricuspid valve will interfere with the pulmonary valve function, compared to the likelihood that a prosthetic mitral valve will interfere with aortic valve function. Still other features of the left heart may need to be taken into account in prosthetic tricuspid valve 300. For example, the coronary sinus flows into right atrium 112, and prosthetic tricuspid valve 300 does not obstruct the coronary sinus. Further, there is an atrioventricular ("AV") node, sometimes referred to as the triangle of Koch, adjacent the native tricuspid valve. It is preferable that the portion of prosthetic heart valve 300 at or adjacent this AV node does not include barbs 390 or other features that would exert excessive pressure on the AV node, otherwise conduction problems could arise.

Figure 8A:
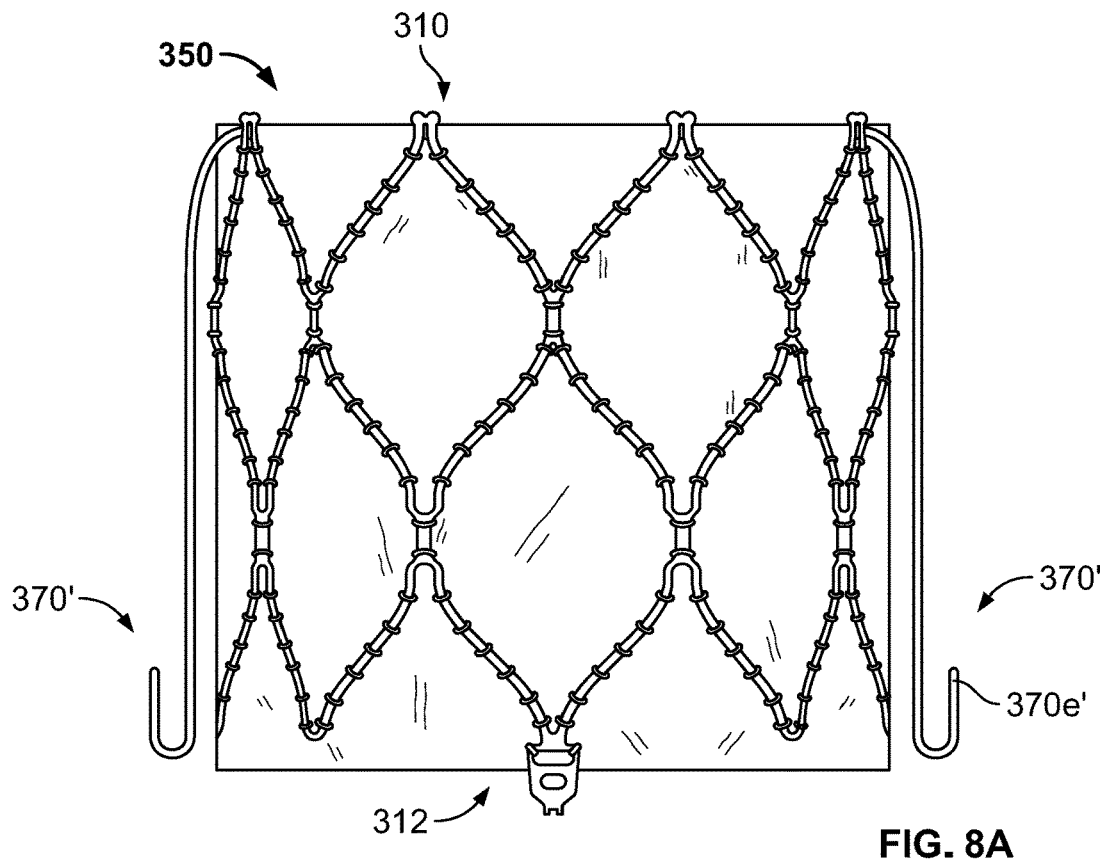
FIG. 8A is a side view of a prosthetic heart valve according to another embodiment of the disclosure.
Figure 8B:
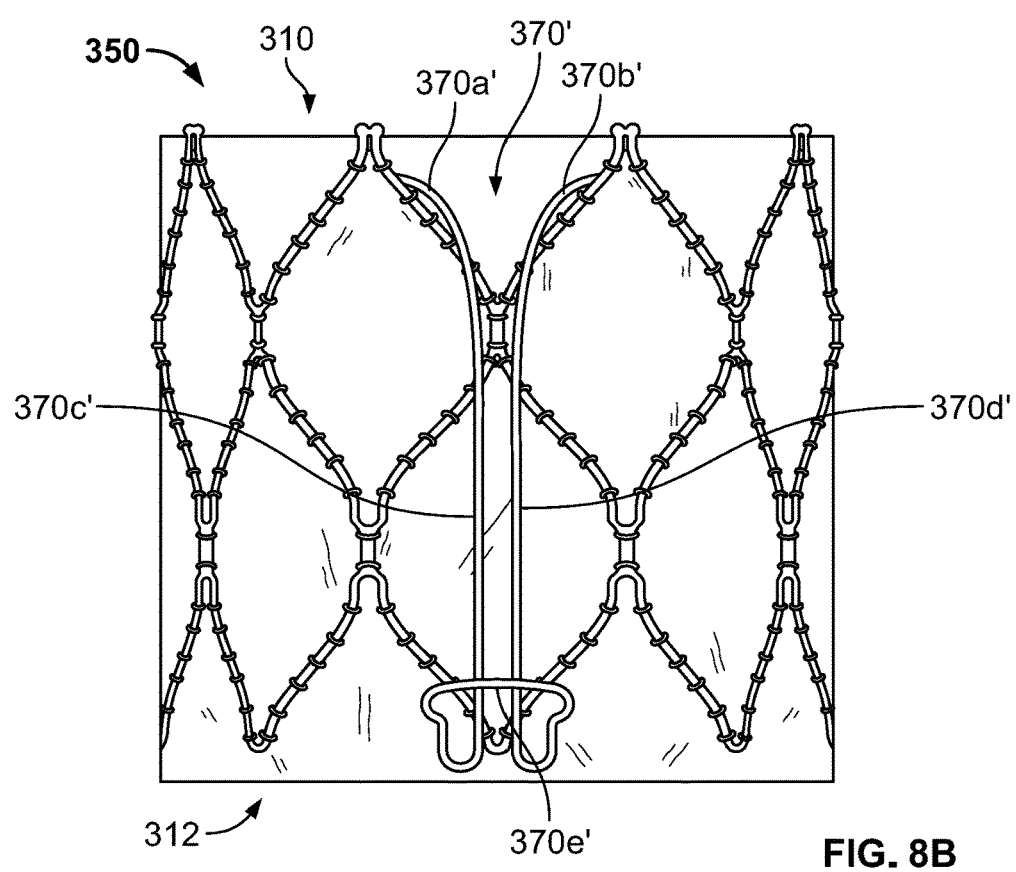
FIG. 8B is a side view of the prosthetic heart valve of FIG. 8A in a different rotational position.

Although anchor arms 370 of prosthetic heart valve 300 are shown and described above as being coupled to outflow end 312 of stent 350, in other embodiments, anchor arms having similar functionality may be coupled to the stent near inflow end 310, or to flange 380. For example, FIG. 8A illustrates stent 350 in the same view as FIG. 4A, with anchor arms 370' coupled to inflow end 310 of stent 350. FIG. 8B shows stent 350 of FIG. 8A rotated about 90 degrees about the longitudinal axis of the stent. Anchor arms 370' may each include a first end 370a' coupled or otherwise attached to an apex of a first cell 354 in the first row of cells 354a at inflow end 310, and a second end 370b' opposite the first end coupled or otherwise attached to an apex of a second cell in the first row of cells at the inflow end, the first and second cells being circumferentially adjacent to each other. The first and second ends 370a', 370b' may transition to elongated center portions 370c', 370d', respectively, that extend toward the outflow end 312 of stent 350. Center portions 370c', 370d' may hook back and join one another to form a tip 370e' that points toward inflow end 310, the tip having a blunted and/or generally circular or oval shape. As best illustrated in FIG. 8A, each anchor arm 370' forms a recess or gap between its tip 370e' and adjacent portions of its center portions 370c', 370d', with the recess or gap intended to receive a portion of the native leaflets 142, 144, 146 of tricuspid valve 140 therein.

It should be understood that the features described above with respect to anchor arms 370 may generally apply with equal force to anchor arms 370'. For example, anchor arms 370' may be formed of any of the materials described above for anchor arms 370, and may include additional tissue and/or fabric layers similar or identical to those described in connection with anchor arms 370. The placement of anchor arms 370' around the circumference of stent may also be similar or identical to that described in connection with anchor arms 370. For example, prosthetic heart valve 300 may include three anchor arms 370' spaced at equal intervals around the circumference of the stent, with the anchor arms functioning to grasp portions of native leaflets 142, 144, 146, preferably at or near their centers, to stabilize the prosthetic heart valve within the annulus of native tricuspid valve 140, and further to reduce movement of the native leaflets. Still further, as with anchor arms 370, the positioning of anchor arms 370' is such that, when prosthetic heart valve 300 is implanted and the anchor arms clip over or otherwise grasp native leaflets 142, 144, 146, there is little or no structure of the prosthetic heart valve positioned beyond the native leaflets toward right ventricle 114. It should be understood that a prosthetic heart valve 300 incorporating anchor arms 370' may also include one or more of flange 380, barbs 390, and parachute 400 described above. Further, although one particular exemplary structure for anchor arms 370' is shown in FIGS. 8A-B, modifications may be suitable. For example, although the portion of each anchor arm that hooks back toward inflow end 310 is illustrated as having a length that is small in relation to the remainder of center portions 370c', 370d', it should be understood that these portions may in some embodiments extend a greater distance back toward the inflow end. For example, in some embodiments, center portions 370c', 370d' may extend from inflow end 310 toward outflow end 312, flip or otherwise hook back toward inflow end 310, and extend a greater distance than shown in FIGS. 8A-B back toward the inflow end prior to transitioning into tip 370e'. With this alternative option, a larger gap or recess may be provided to receive native leaflets 142, 144, 146. Still further, and as noted above, although anchor arms 370' are illustrated as coupled to the inflow end 310 of stent 350, if flange 380 is included in the device, the anchor arms may instead be coupled to the surface of the flange intended to contact the native valve annulus of tricuspid valve 140, preferably at a position near the connection between the flange and the stent.

Prosthetic heart valve 300 is described above as including anchor arms 370 (or anchor arms 370'), flange 380, barbs 390, and parachute 400. However, it should be understood that each feature provides one or more particular functions, and any one of those features may be used in any combination with any one or more of the other features. For example, prosthetic heart valve 300 may include anchor arms 370, flange 380, and parachute 400, but omit barbs 390.

According to one aspect of the disclosure, a prosthetic heart valve comprises: a stent having a collapsed condition, an expanded condition, an inflow end, and an outflow end;

a valve assembly disposed within the stent;

a flange comprising a plurality of braided wires, the flange being coupled to the stent and positioned adjacent the inflow end of the stent in the expanded condition of the stent; and a plurality of anchor arms coupled to the stent, each anchor arm having a first end coupled to the stent adjacent the outflow end of the stent, a second end coupled to the stent adjacent the outflow end of the stent, and center portions extending from the first and second ends toward the inflow end of the stent, the center portions being joined together to form a tip pointing toward the inflow end of the stent in the expanded condition of the stent; and/or the stent includes a first plurality of cells arranged in a first circumferential row adjacent the inflow end of the stent, and a second plurality of cells arranged in a second circumferential row adjacent the outflow end of the stent; and/or the first end of each of the plurality of anchor arms is coupled to a respective first cell in the second circumferential row; and/or the second end of each of the plurality of anchor arms is coupled to a respective second cell in the second circumferential row; and/or for each of the plurality of anchor arms the first cell is circumferentially adjacent the second cell; and/or the stent is formed integrally with the plurality of anchor arms; and/or the plurality of anchor arms includes three anchor arms spaced at substantially equal intervals around a perimeter of the stent; and/or each of the anchor arms is at least partially covered by a first layer of material; and/or the first layer of material is formed of tissue; and/or each of the anchor arms is fully covered by the first layer of material; and/or the first layer of material covers the tips of the anchor arms, and a second layer of material covers the first layer of material; and/or the first layer of material is formed of tissue and the second layer of material is formed of fabric; and/or the flange is coupled to the stent by coupling tubes positioned adjacent the inflow end of the stent; and/or the coupling tubes include barbs having tips that extend radially away from a center longitudinal axis of the stent; and/or the barbs curve away from the outflow end of the stent; and/or the flange includes a first surface adapted to contact a portion of a native valve annulus of a patient when the prosthetic heart valve is in an implanted condition, and a second surface opposite the first surface; and/or a strip of material coupled to the prosthetic heart valve, the strip of material extending around a perimeter of the stent adjacent the inflow end of the stent; and/or the strip of material includes a first edge coupled to the first surface of the flange, and a second edge opposite the first edge, the second edge being positioned nearer a center longitudinal axis of the stent than is the first edge in the expanded condition of the stent, the second edge being coupled to the first surface of the flange at intermittent locations spaced apart from each other; and/or the first edge is substantially continuously coupled to the first surface of the flange so that at least one pocket is formed between the first strip of material and the first surface of the flange, the at least one pocket including a plurality of openings to the at least one pocket between the intermittent locations of attachment of the second edge to the first surface of the flange; and/or an intervening layer of material positioned between the strip of material and the first surface of the flange; and/or the strip of material includes a first edge coupled to the first surface of the flange, and a second edge opposite the first edge, the second edge being positioned nearer a center longitudinal axis of the stent than is the first edge in the expanded condition of the stent, the second edge being coupled to the stent at intermittent locations spaced apart from each other; and/or the first edge is substantially continuously coupled to the first surface of the flange so that at least one pocket is formed between the first strip of material and the first surface of the flange, the at least one pocket including a plurality of openings to the at least one pocket between the intermittent locations of attachment of the second edge to the stent; and/or the strip of material includes a first edge coupled to stent, and a second edge opposite the first edge, the second edge being positioned nearer the outflow end of the stent than is the first, the second edge being coupled to the stent at intermittent locations spaced apart from each other; and/or the first edge is substantially continuously coupled to the stent so that at least one pocket is formed between the first strip of material and stent, the at least one pocket including a plurality of openings to the at least one pocket between the intermittent locations of attachment of the second edge to the stent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic tricuspid heart valve, comprising:
a stent having a collapsed condition, an expanded condition, an inflow end, and an outflow end;
a valve assembly disposed within the stent;
a flange comprising a plurality of braided wires, the flange being coupled to the stent and positioned adjacent the inflow end of the stent in the expanded condition of the stent; and
a plurality of anchor arms coupled to the stent, each anchor arm having a first end coupled to the stent adjacent the outflow end of the stent, a second end coupled to the stent adjacent the outflow end of the stent, and center portions extending from the first and second ends toward the inflow end of the stent, the center portions being joined together to form a tip pointing toward the inflow end of the stent in the expanded condition of the stent,
wherein the stent includes a first plurality of cells arranged in a first circumferential row adjacent the outflow end of the stent,
wherein the first end of each of the plurality of anchor arms is coupled to a respective first cell in the first circumferential row, and
wherein the second end of each of the plurality of anchor arms is coupled to a respective second cell in the first circumferential row.

2. The prosthetic tricuspid heart valve of claim 1, wherein the stent further includes a second plurality of cells arranged in a second circumferential row adjacent the inflow end of the stent.

3. The prosthetic tricuspid heart valve of claim 1, wherein for each of the plurality of anchor arms the first cell is circumferentially adjacent the second cell.

4. The prosthetic tricuspid heart valve of claim 1, wherein the stent is formed integrally with the plurality of anchor arms.

5. The prosthetic tricuspid heart valve of claim 1, wherein the plurality of anchor arms includes three anchor arms spaced at substantially equal intervals around a perimeter of the stent.

6. The prosthetic tricuspid heart valve of claim 1, wherein each of the anchor arms is at least partially covered by a first layer of material.

7. The prosthetic tricuspid heart valve of claim 6, wherein the first layer of material is formed of tissue.

8. The prosthetic tricuspid heart valve of claim 6, wherein each of the anchor arms is fully covered by the first layer of material.

9. The prosthetic tricuspid heart valve of claim 6, wherein the first layer of material covers the tips of the anchor arms, and a second layer of material covers the first layer of material.

10. The prosthetic tricuspid heart valve of claim 9, wherein the first layer of material is formed of tissue and the second layer of material is formed of fabric.

11. The prosthetic tricuspid heart valve of claim 1, wherein the flange is coupled to the stent by coupling tubes positioned adjacent the inflow end of the stent.

12. The prosthetic tricuspid heart valve of claim 11, wherein the coupling tubes include barbs having tips that extend radially away from a center longitudinal axis of the stent.

13. The prosthetic tricuspid heart valve of claim 12, wherein the barbs curve away from the outflow end of the stent.

14. The prosthetic tricuspid heart valve of claim 1, wherein the flange includes a first surface adapted to contact a portion of a native valve annulus of a patient when the prosthetic heart valve is in an implanted condition, and a second surface opposite the first surface.

15. The prosthetic tricuspid heart valve of claim 14, further comprising a strip of material coupled to the prosthetic heart valve, the strip of material extending around a perimeter of the stent adjacent the inflow end of the stent.

16. The prosthetic tricuspid heart valve of claim 15, wherein the strip of material includes a first edge coupled to the first surface of the flange, and a second edge opposite the first edge, the second edge being positioned nearer a center longitudinal axis of the stent than is the first edge in the expanded condition of the stent, the second edge being coupled to the first surface of the flange at intermittent locations spaced apart from each other.

17. The prosthetic tricuspid heart valve of claim 16, wherein the first edge is substantially continuously coupled to the first surface of the flange so that at least one pocket is formed between the first strip of material and the first surface of the flange, the at least one pocket including a plurality of openings to the at least one pocket between the intermittent locations of attachment of the second edge to the first surface of the flange.

18. The prosthetic tricuspid heart valve of claim 17, further comprising an intervening layer of material positioned between the strip of material and the first surface of the flange.

19. The prosthetic tricuspid heart valve of claim 15, wherein the strip of material includes a first edge coupled to the first surface of the flange, and a second edge opposite the first edge, the second edge being positioned nearer a center longitudinal axis of the stent than is the first edge in the expanded condition of the stent, the second edge being coupled to the stent at intermittent locations spaced apart from each other.

20. The prosthetic tricuspid heart valve of claim 19, wherein the first edge is substantially continuously coupled to the first surface of the flange so that at least one pocket is formed between the first strip of material and the first surface of the flange, the at least one pocket including a plurality of openings to the at least one pocket between the intermittent locations of attachment of the second edge to the stent.

21. The prosthetic tricuspid heart valve of claim 15, wherein the strip of material includes a first edge coupled to stent, and a second edge opposite the first edge, the second edge being positioned nearer the outflow end of the stent than is the first, the second edge being coupled to the stent at intermittent locations spaced apart from each other.

22. The prosthetic tricuspid heart valve of claim 21, wherein the first edge is substantially continuously coupled to the stent so that at least one pocket is formed between the first strip of material and stent, the at least one pocket including a plurality of openings to the at least one pocket between the intermittent locations of attachment of the second edge to the stent.

* * * * *